United States Patent
Kornet et al.

(10) Patent No.: US 9,907,962 B2
(45) Date of Patent: Mar. 6, 2018

(54) ARRHYTHMIA PREDICTION BASED ON HEART RATE TURBULENCE

(75) Inventors: Lilian Kornet, Maastricht (NL); Raphael Schneider, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 1468 days.

(21) Appl. No.: 12/608,855

(22) Filed: Oct. 29, 2009

(65) Prior Publication Data

US 2011/0106195 A1    May 5, 2011

(51) Int. Cl.
| | | |
|---|---|---|
| A61N 1/365 | (2006.01) | |
| A61B 5/02 | (2006.01) | |
| A61N 1/362 | (2006.01) | |
| A61B 5/024 | (2006.01) | |
| A61B 5/0402 | (2006.01) | |
| A61B 5/046 | (2006.01) | |
| A61B 5/00 | (2006.01) | |

(52) U.S. Cl.
CPC .............. *A61N 1/3621* (2013.01); *A61B 5/02* (2013.01); *A61B 5/02405* (2013.01); *A61B 5/0402* (2013.01); *A61B 5/046* (2013.01); *A61B 5/6801* (2013.01); *A61B 5/686* (2013.01); *A61N 1/36592* (2013.01)

(58) Field of Classification Search
CPC .......... A61N 1/18; A61N 1/362; A61N 1/365; A61N 1/3621; A61N 1/36592; A61B 5/02; A61B 5/02405; A61B 5/0402; A61B 5/046; A61B 5/6801; A61B 5/686
USPC .......................... 607/25, 14, 17, 44; 600/519
See application file for complete search history.

(56) References Cited

U.S. PATENT DOCUMENTS

| | | |
|---|---|---|
| 4,374,382 A | 2/1983 | Markowitz |
| 5,042,497 A | 8/1991 | Shapland |
| 5,117,824 A | 6/1992 | Keimel et al. |
| 5,437,285 A | 8/1995 | Verrier et al. |
| 5,545,186 A | 8/1996 | Olson et al. |
| 5,749,900 A | 5/1998 | Schroeppel et al. |
| 5,755,738 A | 5/1998 | Gillberg et al. |
| 6,496,722 B1 | 12/2002 | Schmidt |
| 6,920,360 B2 | 7/2005 | Lee et al. |
| 7,079,187 B1 | 7/2006 | Burnes et al. |
| 7,113,829 B2 | 9/2006 | Lindberg et al. |
| 7,155,278 B2 | 12/2006 | King et al. |
| 7,171,256 B1 | 1/2007 | Goode |
| 7,181,277 B1 | 2/2007 | Shelchuk et al. |
| 7,330,750 B2 | 2/2008 | Erkkila et al. |
| 7,580,747 B1 * | 8/2009 | Farazi et al. .................... 607/25 |
| 2002/0138012 A1 | 9/2002 | Hodges et al. |

(Continued)

OTHER PUBLICATIONS http://www.h-r-t.org/hrt/en/publ_old.html, last updated Jun. 8, 2007, 35 pp.

(Continued)

*Primary Examiner* — Carl H Layno
*Assistant Examiner* — Jon Eric C Morales

(57) ABSTRACT

In general, the disclosure describes techniques for predicting the occurrence of an arrhythmia based on an indication of heart rate turbulence. An example method comprises sensing a parameter indicative of heart rate turbulence, measuring heart rate turbulence based on the sensed parameter, and predicting an occurrence of an arrhythmia based on the measured heart rate turbulence.

29 Claims, 10 Drawing Sheets

(56) References Cited

U.S. PATENT DOCUMENTS

| | | |
|---|---|---|
| 2004/0186525 A1 | 9/2004 | Burnes et al. |
| 2005/0234353 A1 | 10/2005 | Xue et al. |
| 2006/0025838 A1 | 2/2006 | Laufer et al. |
| 2007/0208266 A1 | 9/2007 | Hadley |
| 2007/0244402 A1 | 10/2007 | Brockway et al. |
| 2007/0255345 A1 | 11/2007 | Krause |
| 2008/0004672 A1* | 1/2008 | Dalal et al. ............... 607/44 |
| 2008/0033290 A1 | 2/2008 | Saadat et al. |
| 2008/0319254 A1 | 12/2008 | Nikolic et al. |
| 2008/0319332 A1 | 12/2008 | Sornmo et al. |
| 2009/0234409 A1 | 9/2009 | Shuros et al. |
| 2009/0275848 A1 | 11/2009 | Brockway et al. |
| 2009/0281440 A1 | 11/2009 | Farazi et al. |
| 2010/0016913 A1 | 1/2010 | Arcot-Krishnamurthy et al. |

OTHER PUBLICATIONS

Huikuri, "Attenuated recovery of heart rate turbulence early after myocardial infarction identifies patients at high risk for fatal or near-fatal arrhythmic events," Heart Rhythm 2010;7(2):229-35.

Wichterle et al., "Mechanisms Involved in Heart Rate Turbulence," Cardiac Electrophysiology Review 2002;6:262-266.

Savelieva et al., "QT-Interval Turbulence induced by Atrial and Ventricular Extrastimuli in Patients with Ventricular Tachycardia," PACE vol. 28, Jan. 2005, Supplement 1, S187-S192.

Vikman et al., "Heart Rate Turbulence After Atrial Premature Beats Before Spontaneous Onset of Atrial Fibrillation," JACC vol. 45, No. 2, Jan. 18, 2005, pp. 278-284.

Schmidt et al., "Heart-rate turbulence after ventricular premature beats as a predictor of mortality after acute myocardial infarction," The Lancet, vol. 353, Apr. 24, 1999, pp. 1390-1396.

Davies et al., "Relation of Heart Rate and Blood Pressure Turbulence Following Premature Ventricular Complexes to Baroreflex Sensitivity in Chronic Congestive Heart Failure," The American Journal of Cardiology, vol. 87, Mar. 15, 2001, pp. 737-742.

Grimm et al., "Prediction of Major Arrhythmic Events and Sudden Cardiac Death in Dilated Cardiomyopathy," Herz 25, No. 3, 2000, pp. 189-199.

Koyama et al., "Evaluation of Heart-Rate Turbulence as a New Prognostic Marker in Patients With Chronic Heart Failure," Circ. J. 2002; 66:902-907.

Iwasa, "Abnormal Heart Rate Turbulence Predicts the Initiation of Ventricular Arrhythmias," PACE vol. 26, pp. 1189-1197, Nov. 2005.

Grimm et al., "Heart-Rate Turbulence following Ventricular Premature Beats in Healthy Controls," A.N.E. vol. B, No. 2, pp. 127-131, Apr. 2003.

Lindgren et al., "Heart Rate Turbulence after Ventricular and Atrial Premature Beats in Subjects without Structural Heart Disease," Journal of Cardiovascular Electrosphysiology, vol. 14, No. 5, May 2003, pp. 447-452.

Sestito et al., "Differences in Heart Rate Turbulence Between Patients With Coronary Artery Disease and Patients With Ventricular Arrhythmias But Structurally Normal Hearts," Am J. Cardiol., 2004;93:1114-1118.

Schwab et al., "Determinants of Heart Rate Turbulence after Ventricular Premature Beats in Healthy Volunteers," Hellenic J. Cardiol. 46:31-34, 2005

Watanabe, "Heart Rate Turbulence Slope Reduction in Imminent Ventricular Tachartythmia and is Implications," J Cardiovasc. Electrophysiol., Jul. 2006, 17(7):735-740.

http://www.h-r-t.com/hrt/en/index.html, last updated Mar. 27, 2007, 1 pg.

http://www.h-r-t.com/hrt/en/publ.hmtl, last updated Oct. 16, 2008, 24 pp.

U.S. Appl. No. 12/765,482, entitled "Cardiac Risk Stratification," filed Apr. 22, 2010, by Marc D. Messier.

Medscape Today, "Time Domain Measures of HRV," J Cardiovasc Electrophysiol 2006; 17(6):691-694.

Stiles, "CARISMA: Markers of Autonomic Function Stratify Post-MI, Low-LVEF Sudden-Death Risk," found online at http://www.medscape.com/viewarticle556606, May 16, 2007, 2 pp.

Grimm, "Prognostic Significance of Heart Rate Turbulence Following Ventricular Premature Beats in Patients with Idiopathic Dilated Cardiomyopathy," Journal of Cardiovascular Electrophysiology, vol. 14 No. 8, pp. 819-824, Aug. 2003.

Huikuri et al., "Prediction of Fatal or Near-Fatal Ventricular Tachyarrhythmias in Patients with Depressed Left Ventricular Function after Acute Myocardial Infarction: The CARISMA Study," Medtronic Scientia, Sep. 2, 2007, 1 pg.

PowerPoint presentation by Thomsen et al., "Cardiac Arrhythmias and Risk Stratification in Patients with Low Ejection Fraction after Acute Myocardial Infarction: The CARISMA Study," presented at Heart Rhythm Society 2007 Scientific Sessions, May 10, 2007, 26 pp.

PowerPoint presentation by Thomsen et al., "CARISMA: Prognostic power of autonomic and electrophysiology measures of sudden-death risk," presented at Heart Rhythm Sociely 2007 Scientific Sessions, May 10, 2007, Denver CO., 1 pg.

Huikuri, "Recovery of Cardiac Autonomic Dysfunction after Acute Myocardial Infarction: a potential Predictor of Fatal or Near-Fatal Arrhythmic Events," abstract of presentation from 2006 American Heart Association conference, Nov. 8-12, 2008, 1 pg.

U.S. Appl. No. 61/122,029, filed Dec. 12, 2006 entitled "Method of Risk Stratification of Ventricular or Atrial Arrhythmias Based Upon Multiple Indicators."

(PCT/US2010/051252) PCT Notification of Transmittal of the International Search Report and the Written Opinion of the International Searching Authority.

Guzik, et al., "A Phenomenon of Heart-Rate Turbulence, Its Evaluation, and Prognostic Value", Article, 2002, pp. 256-261, Cardiac Electrophysiology Review, 2002 Kluwer Academic Publishers, Manufactured in the Netherlands.

Schmidt, et al., "Heart-rate turbulence after ventricular premature beats as a predictor of mortality after acute myocardial infarction", The Lancet vol. 353 Apr. 24, 1999, p. 1390-1396.

\* cited by examiner

ARRHYTHMIA PREDICTION BASED ON HEART RATE TURBULENCE

TECHNICAL FIELD

The disclosure relates to medical devices and, more particularly, to medical devices that sense electrical signals within a patient.

BACKGROUND

A variety of medical devices for delivering a therapy and/or monitoring a physiological condition have been used clinically or proposed for clinical use in patients. Examples include medical devices that deliver therapy to and/or monitor conditions associated with the heart, muscle, nerve, brain, stomach or other organs or tissue. Some medical devices may employ electrodes for the delivery of electrical stimulation to such organs or tissues, electrodes for sensing electrical signals within the patient, which may be generated by such organs or tissue, and/or other sensors for sensing physiological parameters of a patient.

Implantable medical devices, such as cardiac pacemakers or implantable cardioverter-defibrillators, for example, provide therapeutic electrical stimulation to the heart via electrodes carried by one or more implantable leads. The electrical stimulation may include signals such as pulses or shocks for pacing, cardioversion or defibrillation. In some cases, an implantable medical device senses intrinsic depolarizations of the heart, and controls delivery of stimulation signals to the heart based on the sensed depolarizations. Upon detection of an abnormal rhythm, such as bradycardia, tachycardia or fibrillation, the implantable medical device may deliver an appropriate electrical stimulation signal or signals to restore or maintain a more normal rhythm. For example, in some cases, an implantable medical device delivers pacing pulses to the heart of the patient upon detecting tachycardia or bradycardia, and delivers cardioversion or defibrillation shocks to the heart upon detecting fibrillation.

SUMMARY

In general, the disclosure describes techniques for predicting the occurrence of an arrhythmia based on an indication of heart rate turbulence (HRT). HRT is a physiological response of the heart and may occur in response to abnormal heart beats as the body attempts to restore itself to its normal state. A medical device may identify abnormal heart beats and measure HRT resulting from the identified abnormal heart beats. If too few abnormal heart beats are occurring naturally, the medical device may induce an abnormal heart beat, e.g., by providing one or more pacing pulses to the heart. If the measured HRT, e.g., the measured HRT related parameter, deviates from a baseline by at least a threshold amount, the medical device may predict the occurrence of an arrhythmia. HRT measurements may be derived based on heart rate, e.g., based on time intervals between heart beats. Heart rate may be derived from an electrogram or electrocardiogram, but also from pressure, impedance, movement, sound, flow, optic, or chemical signals. The medical device may provide a therapy configured to prevent the predicted arrhythmia from occurring, reduce an effect of the arrhythmia, or terminate the arrhythmia.

In one example, the disclosure is directed to a method comprising sensing a parameter indicative of heart rate turbulence wherein the sensed parameter comprises cardiac contractility, deriving a plurality of values of an interval between cardiac contractions from the sensed parameter measuring heart rate turbulence based on the sensed parameter, and predicting an occurrence of an arrhythmia based on the measured heart rate turbulence wherein measuring heart rate turbulence comprises calculating heart rate turbulence based on the interval values.

In another example, the disclosure is directed to a system comprising a sensing module that monitors a parameter indicative of heart rate turbulence wherein the sensed parameter comprises cardiac contractility and a processor that derives a plurality of values of an interval between cardiac contractions from the sensed parameter, measures heart rate turbulence based on the sensed parameter and predicts an occurrence of an arrhythmia based on the measured heart rate turbulence wherein measuring heart rate turbulence comprises calculating heart rate turbulence based on the interval values.

In another example, the disclosure is directed to a computer-readable medium comprising instructions for causing a programmable processor to control sensing of a parameter indicative of heart rate turbulence wherein the sensed parameter comprises cardiac contractility, derive a plurality of values of an interval between cardiac contractions from the sensed parameter, measure heart rate turbulence based on the sensed parameter, and predict an occurrence of an arrhythmia based on the measured heart rate turbulence wherein measuring heart rate turbulence comprises calculating heart rate turbulence based on the interval values.

In another example, the disclosure is directed to a system comprising means for sensing a parameter indicative of heart rate turbulence wherein the sensed parameter comprises cardiac contractility, means for deriving a plurality of values of an interval between cardiac contractions from the sensed parameter and for measuring heart rate turbulence based on the sensed parameter, and means for predicting an occurrence of an arrhythmia based on the measured heart rate turbulence.

The details of one or more examples of the invention are set forth in the accompanying drawings and the description below. Other features, objects, and advantages of the invention will be apparent from the description and drawings, and from the claims.

DETAILED DESCRIPTION

In general, the disclosure describes techniques for predicting the occurrence of an arrhythmia based on an indication of heart rate turbulence (HRT). HRT is a physiological response of the heart and may occur in response to premature atrial contractions (PACs), premature ventricular contractions (PVCs), or other abnormal heart beats as the body attempts to restore itself to its normal state.

A medical device may identify PACs, PVCs, and/or other abnormal heart beats and measure HRT resulting from the identified abnormal heart beats. If too few abnormal heart beats are occurring naturally, the medical device may induce an abnormal heart beat, e.g., by providing one or more pacing pulses to the heart.

If the measured HRT deviates from a baseline by at least a threshold amount, the medical device may predict the occurrence of an arrhythmia. In general, the medical device may deliver one or more therapies in response to predicting the occurrence of an arrhythmia. In some examples, the medical device may provide a therapy prior to the occurrence of an arrhythmia to help prevent the predicted arrhythmia from occurring. Example therapies may include overdrive pacing, spinal cord stimulation, vagal stimulation, baroreflex stimulation, deep brain stimulation, sympathetic inhibition, and/or cardiac ganglion stimulation. As another example, the medical device may deliver a therapy configured to reduce an effect of the arrhythmia, such as conduction of the arrhythmia from the atrium to the ventricle. For example, the medical device may deliver atrio-ventricular (AV) nodal stimulation configured to help prevent a supraventricular tachyarrhythmia from being conducted to the ventricles.

As yet another example, the medical device may deliver a therapy configured to terminate the predicted arrhythmia. For example, the medical device may deliver antitachycardia pacing. The medical device may additionally or alternatively charge a therapy delivery circuit for delivery of a cardioversion or defibrillation shock in response to predicting the occurrence of an arrhythmia. In this manner, the therapy delivery circuit may be at least partially charged upon onset of the tachyarrhythmia. This may help reduce the time between arrhythmia onset and therapy delivery.

Figure 1:
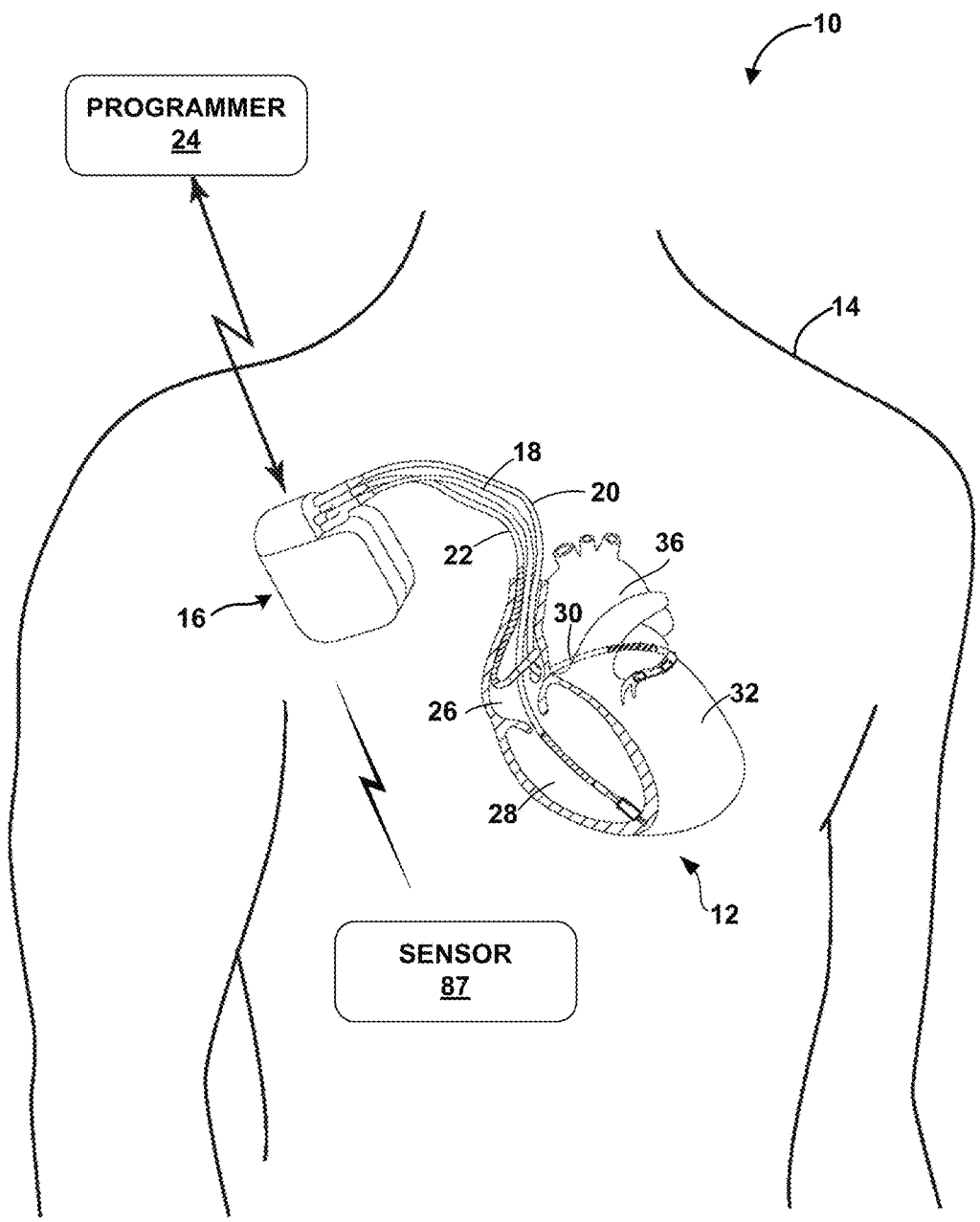
FIG. 1 is a conceptual drawing illustrating an example system that includes an implantable medical device (IMD) coupled to implantable medical leads.

FIG. 1 is a conceptual diagram illustrating an example system 10 that may be used for sensing of physiological parameters of patient 14 and/or to provide therapy to heart 12 of patient 14. Therapy system 10 includes IMD 16, which is coupled to leads 18, 20, and 22, and programmer 24. System 10 may also include one or more sensors 87, e.g., in wired or wireless communication with IMD 16. IMD 16 may be, for example, an implantable pacemaker, cardioverter, and/or defibrillator that provides electrical signals to heart 12 via electrodes coupled to one or more of leads 18, 20, and 22.

Although an implantable medical device and delivery of electrical stimulation to heart 12 are described herein as examples, the techniques for predicting the occurrence of an arrhythmia of this disclosure may be applicable to other medical devices and/or other therapies. In general, the techniques described in this disclosure may be implemented by any medical device, e.g., implantable or external, that senses a parameter indicative of HRT, or any one or more components of a system including such a medical device. As one alternative example, IMD 16 may be a cardiac monitoring device that monitors one or more signals from heart 12 of patient 14 but may not deliver a therapy to heart 12 or patient 14. One example of a cardiac monitor is a Reveal® monitor, commercially available from Medtronic Inc. of Minneapolis, Minn. As another example, an ambulatory cardiac monitor may be used, such as a monitor that generates a signal indicative of cardiac depolarization or contraction. Such a monitor may be external and may be used in an ambulance, intensive care unit, and/or other clinical settings in which the patient may be vulnerable to arrhythmias. Such an external cardiac monitor may include electrodes to detect electrical cardiac depolarizations, e.g., R-R intervals, or other sensors capable of sensing mechanical cardiac contractions (sensing cardiac contractility), e.g., a pressure sensor from which R-R intervals may be derived based on the distance between pressure peaks. As described in further detail below, R-R interval values may be used to calculate a heart rate turbulence related parameter.

In some examples, therapy system 10 may include a neurostimulator. For example, IMD 16 may be a neurostimulator that delivers electrical stimulation to and/or monitors conditions associated with the brain, spinal cord, or neural tissue of patient 14. In other examples, therapy system 10 may include a neurostimulator in addition to IMD 16. In some examples, IMD 16 may provide cardiac stimulation to heart 12 and neurostimulation to patient 14, e.g., to the brain, spinal cord, or neural tissue of patient 16

In the example of FIG. 1, leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, therapy system 10 may additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, therapy system 10 may additionally or alternatively include temporary or permanent epicardial or subcutaneous leads, instead of or in addition to transvenous, intracardiac leads 18, 20 and 22. Such leads may be used for one or more of cardiac sensing, pacing, or cardioversion/defibrillation.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. As one example, IMD 16 may provide antitachycardia pacing pulses in response to detect a tachycardia based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

IMD 16 may measure HRT and may predict the occurrence of an arrhythmia based on the measured HRT. In some examples, IMD 16 may measure HRT based on the electrical signals sensed within heart 12. In some examples, IMD 16 may provide a therapy in response to predicting the occurrence of an arrhythmia. For example, IMD 16 may initiate overdrive pacing in one or more atria and/or ventricles of heart 12. As another example, IMD 16 may deliver antitachycardia pacing in response to predicting the occurrence of an arrhythmia. In examples in which IMD 16 is configured to deliver neurostimulation, IMD 16 may deliver stimulation signals to or proximate to the spinal cord, vagus nerve, or other neural targets to help adjust autonomic activity. The therapy that IMD 16 delivers in response to predicting the occurrence of an arrhythmia may be configured to help prevent the predicted arrhythmia from occurring, reduce an effect of the arrhythmia, or terminate the arrhythmia.

In other examples, one or more of sensor 87 sense cardiac contractions of heart 12. IMD 16 may measure HRT based on the signals sensed by sensors 87, and predict the occurrence of an arrhythmia based on the measured HRT. Examples of sensors 87 that may generate a signal indicative of cardiac contraction include a intracardiac or intravascular, e.g., arterial, pressure sensor, an accelerometer or other sensor capable of detecting heart or blood sounds, vibrations, or motion, an intra-cardiac or intra-arterial impedance, optical or ultrasonic sensor capable or detecting changes in blood flow associated with cardiac contractions, or an optical sensor capable of detecting oxygen saturation changes associated with cardiac contractions.

In some examples, programmer 24 comprises a handheld computing device, computer workstation, or networked computing device. Programmer 24 may include a user interface that receives input from a user. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as HRT, intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16. In some examples, this information may be presented to the user as an alert.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
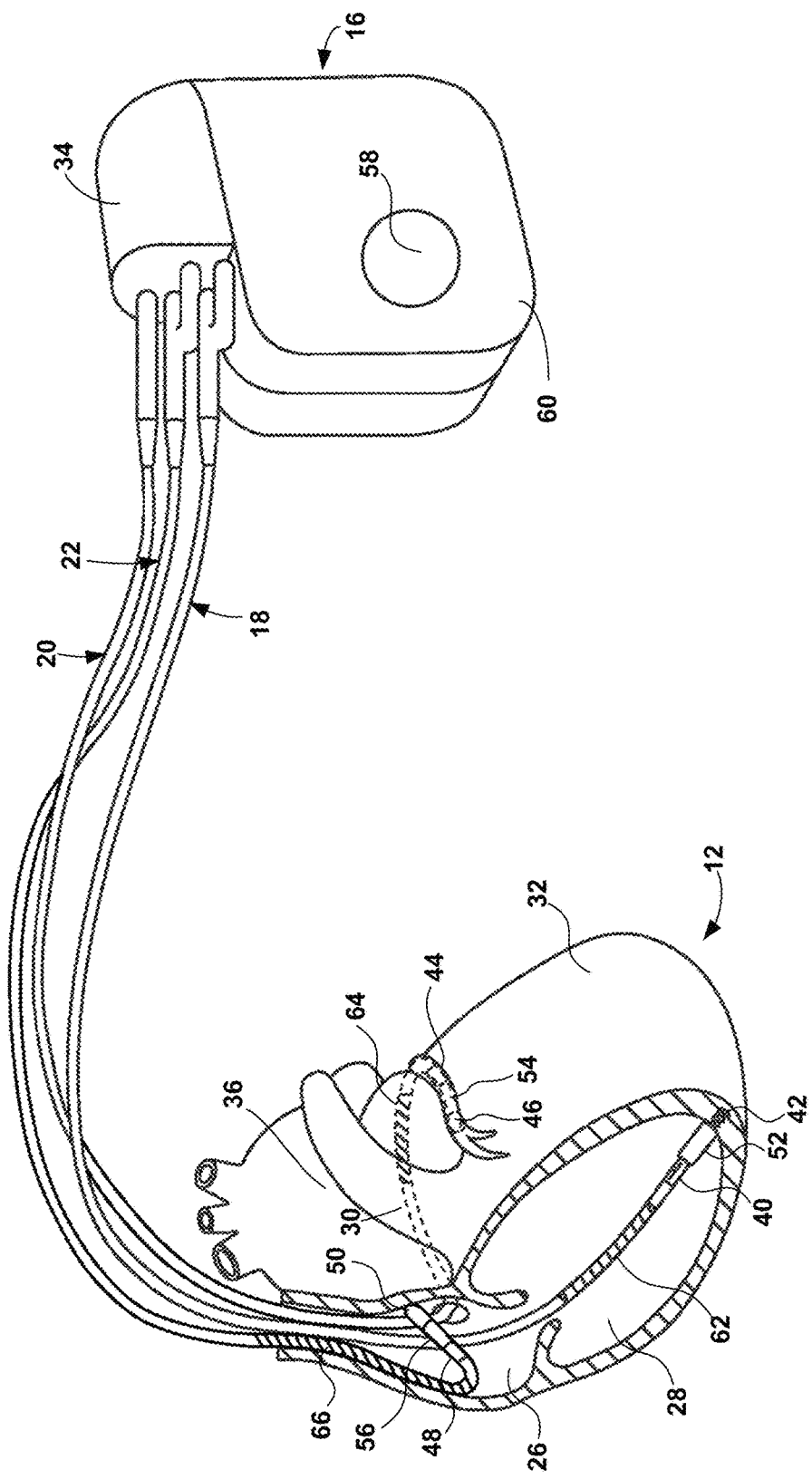
FIG. 2 is a conceptual drawing illustrating the example IMD and leads of FIG. 1 in conjunction with a heart.

FIG. 2 is a conceptual diagram illustrating IMD 16 and leads 18, 20 and 22 of therapy system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. In examples in which an IMD comprises a monitor, the IMD may not be coupled to leads, and instead may include a plurality of housing electrodes. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. In some examples, IMD 16 delivers one or more pacing pulses configured to induce an abnormal heartbeat to facilitate measurement of HRT. In some examples, IMD 16 delivers pacing pulses to right ventricle 28 and/or left ventricle 32 based on sensed atrial activity. When IMD 16 senses a parameter indicative of HRT, IMD 16 may not permit delivery of pacing to right atrium 26 and/or left atrium 36 to help ensure that the timing of heartbeats are controlled by the autonomic nervous system and not artificially controlled by IMD 16.

Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of therapy system 10 illustrated in FIGS. 1 and 2 is merely one example. In other examples, a therapy system may include epicardial leads, patch electrodes, and/or subcutaneous electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver pacing and/or defibrillation pulses and other therapies to heart 12 via percutaneous leads that extend through the skin of patient 14 to a variety of positions within or outside of heart 12.

Figure 3:
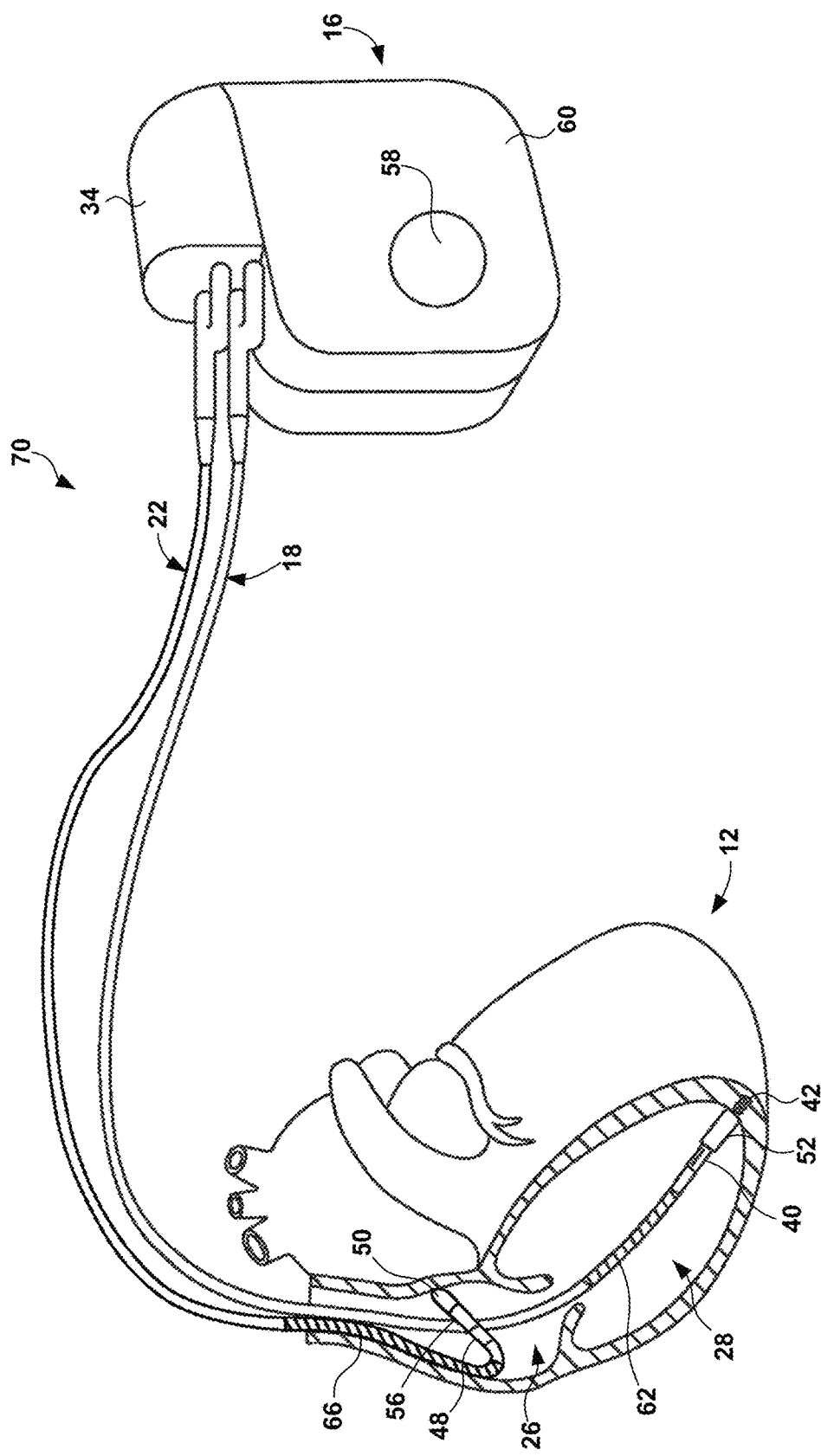
FIG. 3 is a conceptual drawing illustrating the example IMD of FIG. 1 coupled to a different configuration of implantable medical leads in conjunction with a heart.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3. Any electrodes located on these additional leads may be used in sensing and/or stimulation configurations.

Additionally, as previously mentioned, IMD 16 need not deliver therapy to heart 12. In some examples, IMD 16 is not coupled to leads, and instead monitors cardiac electrical signals via a plurality of housing electrodes. An example of such an IMD is the aforementioned Reveal® monitor. In general, this disclosure may be applicable to any medical device, e.g., implantable or external, that senses a parameter indicative of HRT.

FIG. 3 is a conceptual diagram illustrating another example system 70, which is similar to system 10 of FIGS. 1 and 2, but includes two leads 18, 22, rather than three leads. Leads 18, 22 are implanted within right ventricle 28 and right atrium 26, respectively. System 70 shown in FIG. 3 may be useful for sensing cardiac electrical signals, providing defibrillation and pacing pulses to heart 12, measuring HRT based on the electrical signals sensed within heart 12, and predicting the occurrence of an arrhythmia based on the measured HRT, as described herein with respect to system 10.

Figure 4:
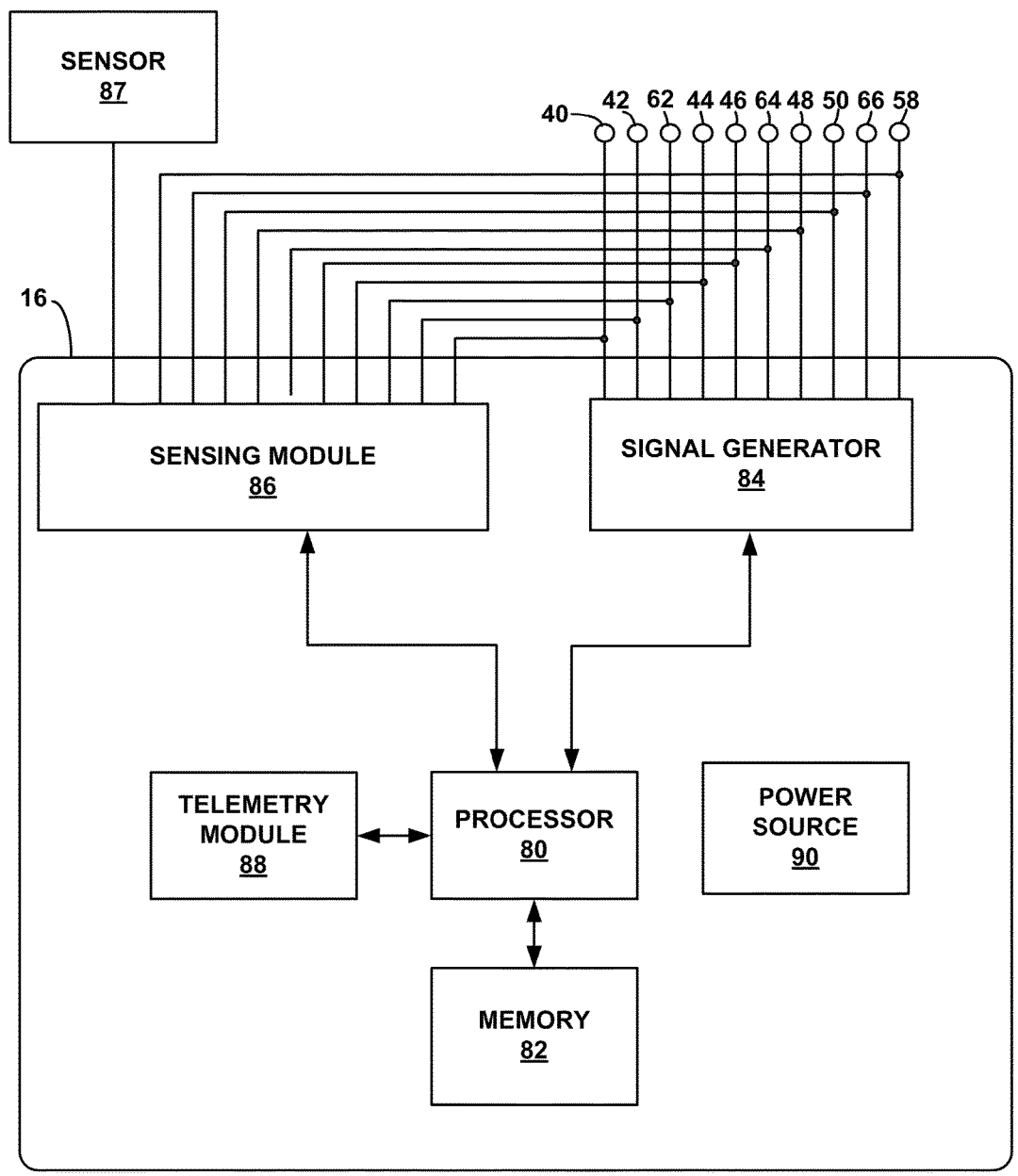
FIG. 4 is a functional block diagram illustrating an example configuration of the IMD of FIG. 1.

FIG. 4 is a functional block diagram illustrating an example configuration of IMD 16. In the illustrated example, IMD 16 includes a processor 80, memory 82, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a selected one or more of therapy programs, which may be stored in memory 82. For example, processor 80 may control stimulation generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Sensing module 86 monitors signals from at least one of electrodes 40, 42, 44, 46, 48, 50, 58, 62, 64 or 66 in order to monitor electrical activity of heart 12. Sensing module 86 may also include a switch module to select which of the available electrodes are used to sense the heart activity, depending upon which electrode combination is used in the current sensing configuration. In some examples, processor 80 may select the electrodes that function as sense electrodes, i.e., select the sensing configuration, via the switch module within sensing module 86. Processor 80 may control the functionality of sensing module 86 by providing signals via a data/address bus.

Sensing module 86 may include one or more detection channels, each of which may comprise an amplifier. The detection channels may be used to sense the cardiac signals. Some detection channels may detect events, such as R- or P-waves, and provide indications of the occurrences of such events to processor 80. One or more other detection channels may provide the signals to an analog-to-digital converter, for processing or analysis by processor 80. In response to the signals from processor 80, the switch module within sensing module 86 may couple selected electrodes to selected detection channels.

For example, sensing module 86 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 80 then uses that detection in measuring frequencies of the sensed events. Different narrow band channels of sensing module 86 may have distinct functions. For example, some various narrow band channels may be used to sense either atrial or ventricular events.

In one example, at least one narrow band channel may include an R-wave amplifier that receives signals from the sensing configuration of electrodes 40 and 42, which are used for sensing and/or pacing in right ventricle 28 of heart 12. Another narrow band channel may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a wide band channel which may comprise an amplifier with a relatively wider pass band than the R-wave or P-wave amplifiers. Signals from the selected sensing electrodes that are selected for coupling to this wide-band amplifier may be converted to multi-bit digital signals by an analog-to-digital converter (ADC) provided by, for example, sensing module 86 or processor 80. In some examples, processor 80 may store the digitized versions of signals from the wide band channel in memory 82 as electrograms (EGMs). In some examples, processor 80 may employ digital signal analysis techniques to characterize the digitized signals from the wide band channel to, for example detect and classify the patient's heart rhythm. Processor 80 may detect and classify the patient's heart rhythm by employing any of the numerous signal processing methodologies known in the art.

Sensing module 86 may also include one or more sensors 87 separate from electrodes 40, 42, 44, 46, 48, 50, 58, 62, 64 and 66. For example, one or more sensors 87 may be coupled to IMD 16 via one or more of leads 18, 20 and 22 or may be in wireless communicate with IMD 16. Via a signal generated by sensor 87, processor 80 may monitor one or more physiological parameters indicative of cardiac contraction, autonomic tone, heart failure, ejection fraction, and/or HRT. Examples of sensors 87 that may generate a signal indicative of cardiac contraction include a intracardiac or intravascular pressure sensor, an accelerometer or other sensor capable of detecting heart or blood sounds, vibrations, or motion, an intra-cardiac or intra-arterial impedance, optical or ultrasonic sensor capable or detecting changes in blood flow associated with cardiac contractions, or an optical sensor capable of detecting oxygen saturation changes associated with cardiac contractions. Processor 80 may detect cardiac contractions based on signals from one or more sensors 87, and determine HRT based on the intervals between contractions in a manner similar to determining heart rate variability based on P-P or R-R intervals.

Processor 80 may also identify abnormal heart beats based on signals sensed by sensing module 86. For example, as previously described, sensing module 86 may include a narrow band channel that includes an R-wave amplifier or P-wave amplifier to detect R-wave or P-waves, or otherwise detects cardiac depolarizations. Processor 80 may monitor intervals between detected depolarizations, e.g., R-R intervals, and identify abnormal heart beats based on changes in the intervals. In other examples, processor 80 may identify abnormal heartbeats by identifying changes in heartbeat morphology, e.g., by analyzing an EGM signal sensed by sensing module 86.

Since HRT occurs when the body attempts to restore itself to its normal state, identifying abnormal heartbeats may be particularly useful in monitoring HRT. Sensing module 86 may sense a parameter indicative of HRT. In some examples, as described in further detail below, processor 80 may measure HRT based on the intervals between detected depolarizations. In some examples, processor 80 may identify abnormal heart beats and calculate HRT resulting from the identified abnormal heart beats. For example, processor 80 may monitor intervals between depolarizations to identify abnormal heart beats. Processor 80 may calculate HRT using one or more intervals prior to and/or subsequent to an identified abnormal heart beat to calculate HRT resulting from the identified abnormal heart beat.

If too few abnormal heart beats are occurring naturally, processor 80 may control signal generator 84 induce an abnormal heartbeat. For example, processor 80 may monitor a number of naturally occurring abnormal heartbeats during an observation period. If the number of naturally occurring abnormal heartbeats is below a threshold value, processor 80 may control signal generator 84 to provide one or more signals to heart 12 to induce an abnormal heartbeat. For example, signal generator 84 may provide one or more pacing pulses configured to induce a PAC, PVC, or other abnormal heartbeat. As one example, processor 80 may control signal generator 84 to stimulate approximately ten abnormal heartbeats with approximately twenty to approximately twenty five intrinsic heartbeats separating each abnormal heartbeat. Processor 80 may control signal generator 84 to induce the abnormal heartbeats at a specified time of day, e.g., while patient 14 is sleeping or another time of day when the abnormal heartbeats may go unnoticed. Inducing abnormal heart beats when too few abnormal heart beats are naturally occurring may allow processor 80 to monitor HRT as the body is restoring itself to a normal state in response to the induced abnormal beats.

If the measured HRT deviates from a baseline by at least a threshold amount, processor 80 may predict the occurrence of an arrhythmia. The baseline may be a general baseline used for all patients or may be specific to patient 14. For example, processor 80 may store, e.g., in memory 82, values of HRT measured over time and track deviations from previous recordings, e.g., a running average of all previous recordings or a recent subset of previous recordings.

In some examples, processor 80 may control signal generator 84 to provide a therapy to help prevent the predicted arrhythmia from occurring, reduce an effect of the arrhythmia, or terminate the arrhythmia. For example, processor 80 may control signal generator 84 to deliver overdrive pacing, antitachycardia pacing, spinal cord stimulation, vagal stimulation, baroreflex stimulation, deep brain stimulation, sympathetic inhibition, and/or cardiac ganglion stimulation. Signal generator 84 may deliver a different type of therapy based on how the measured heart rate turbulence varies from the baseline. Therapy may also be titrated based on the deviation from baseline. Therapy may not necessarily be prevention therapy, but may also be directed to the reduction of symptoms. For example, with AV-nodal stimulation, arrhythmias in the atria may be prevented from conducting to the ventricles and becoming symptomatic. Additionally, the therapy may also be used to help provide faster termination of ventricular arrhythmias. For example, processor 80 may initiate charging of therapy delivery circuitry, e.g., capacitors for delivery of defibrillation, upon predicting an arrhythmia. As a result the time between arrhythmia detection and therapy delivery may be shortened, since the therapy deliver circuitry may be at least partially charged in advance.

If IMD 16 is configured to generate and deliver pacing pulses to heart 12, processor 80 may define intervals, such as atrial and ventricular pacing escape intervals, and refractory periods during which sensed P-waves and R-waves are ineffective to restart timing of the escape intervals, as well as the pulse widths of the pacing pulses. As another example, processor 80 may define a blanking period, and provide signals to sensing module 86 to blank one or more channels, e.g., amplifiers, for a period during and after delivery of electrical stimulation to heart 12. The durations of these intervals may be determined by processor 80 in response to stored data in memory 82. Processor 80 may also determine the amplitude of the cardiac pacing pulses.

Processor 80 may maintain interval counters, which may be escape interval counters in examples in which pacing therapy is delivered. Processor 80 may reset such interval counters upon sensing of R-waves and P-waves by detection channels of sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may also reset the interval counters upon the generation of pacing pulses by signal generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a suspected tachyarrhythmia event, such as ventricular fibrillation or ventricular tachycardia. In some examples, a portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

Processor 80 may also use the intervals from the arrhythmia detection module to detect abnormal heartbeats. For example, processor 80 may detect an abnormal heartbeat if the interval falls below a threshold, regardless of whether the interval length is detected for a certain number of consecutive cycles, for a certain percentage of cycles within a running window, or a running average for a certain number of cardiac cycles.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In addition, processor 80 may transmit information regarding HRT, predicted arrhythmias, and/or therapy delivered in response to a predicted arrhythmia to programmer 24 via telemetry module 88. For example, processor 80 may provide an alert regarding any predicted arrhythmia, suggest a response to a predicted arrhythmia, or provide an EGM or other sensed signal for prediction of the occurrence of an arrhythmia to programmer 24 via telemetry module 88. Processor 80 may also receive information regarding predicted arrhythmias or responses to such predicted arrhythmias from programmer 24 via telemetry module 88.

In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician.

Figure 5:
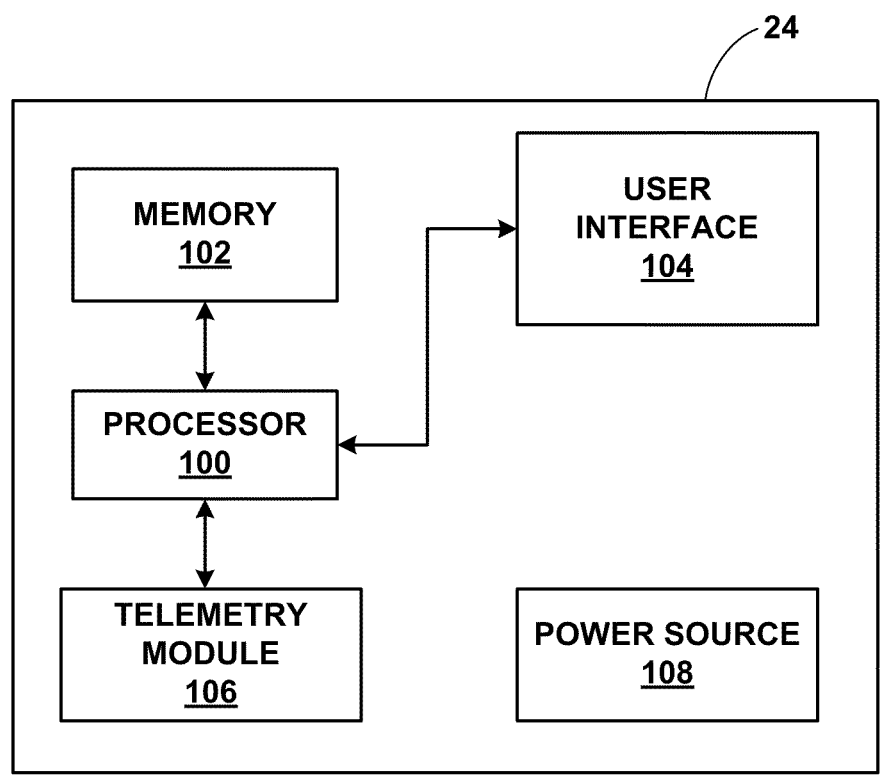
FIG. 5 is a functional block diagram illustrating an example configuration of an external programmer that facilitates user communication with the IMD.

FIG. 5 is functional block diagram illustrating an example configuration of programmer 24. As shown in FIG. 5, programmer 24 may include a processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 104, which may include display to present graphical user interface to a user, and a keypad or another mechanism for receiving input from a user.

The user may also use programmer 24 to adjust or control the monitoring of abnormal heartbeats and HRT performed by IMD 16. In addition, the user may receive an alert from IMD 16 indicating a predicted arrhythmia via programmer 24. The user may respond to IMD 16 by suggesting a response to the predicted arrhythmia. Alternatively, IMD 16 may automatically suggest a response to the predicted arrhythmia. Programmer 24 may prompt the user to confirm the response.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 100 of programmer 24 and/or one or more processors of one or more networked computers may perform all or a portion of the techniques described herein with respect to processor 80 and IMD 16. For example, processor 100 or another processor may receive an EGM or other sensed signal for predicting the occurrence of arrhythmias based on HRT.

Figure 6:
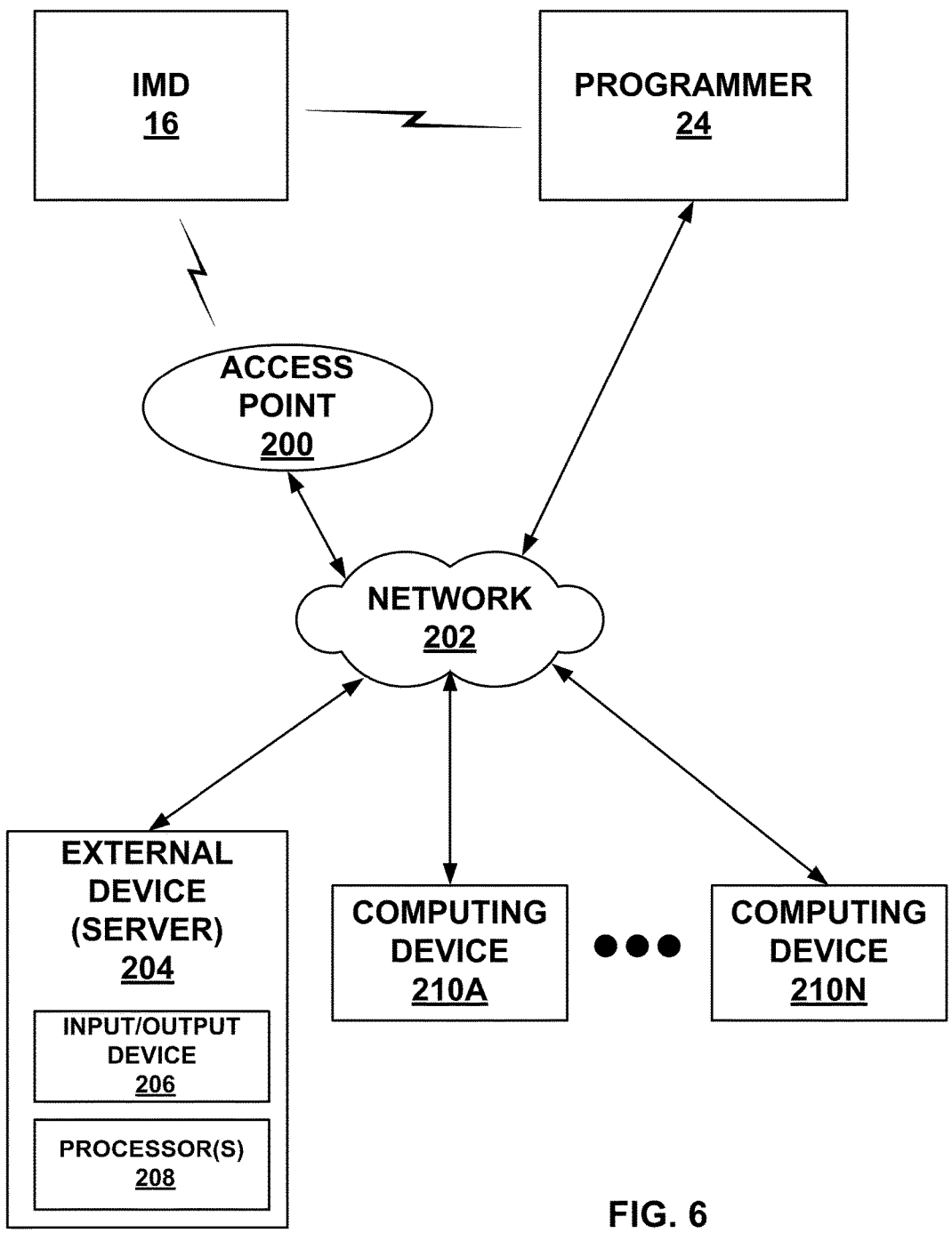
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 6, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some examples, server 204 or computing devices 210 may control or perform any of the various functions or operations described herein, e.g., control monitoring of HRT by IMD 16.

In some cases, server 204 may be configured to provide a secure storage site for archival of HRT information that has been collected from IMD 16 and/or programmer 24. Network 202 may comprise a local area network, wide area network, or global network, such as the Internet. In some cases, programmer 24 or server 204 may assemble HRT information in web pages or other documents for viewing by and trained professionals, such as clinicians, via viewing terminals associated with computing devices 210. The system of FIG. 6 may be implemented, in some aspects, with general network technology and functionality similar to that provided by the Medtronic CareLink® Network developed by Medtronic, Inc., of Minneapolis, Minn.

Figure 7:
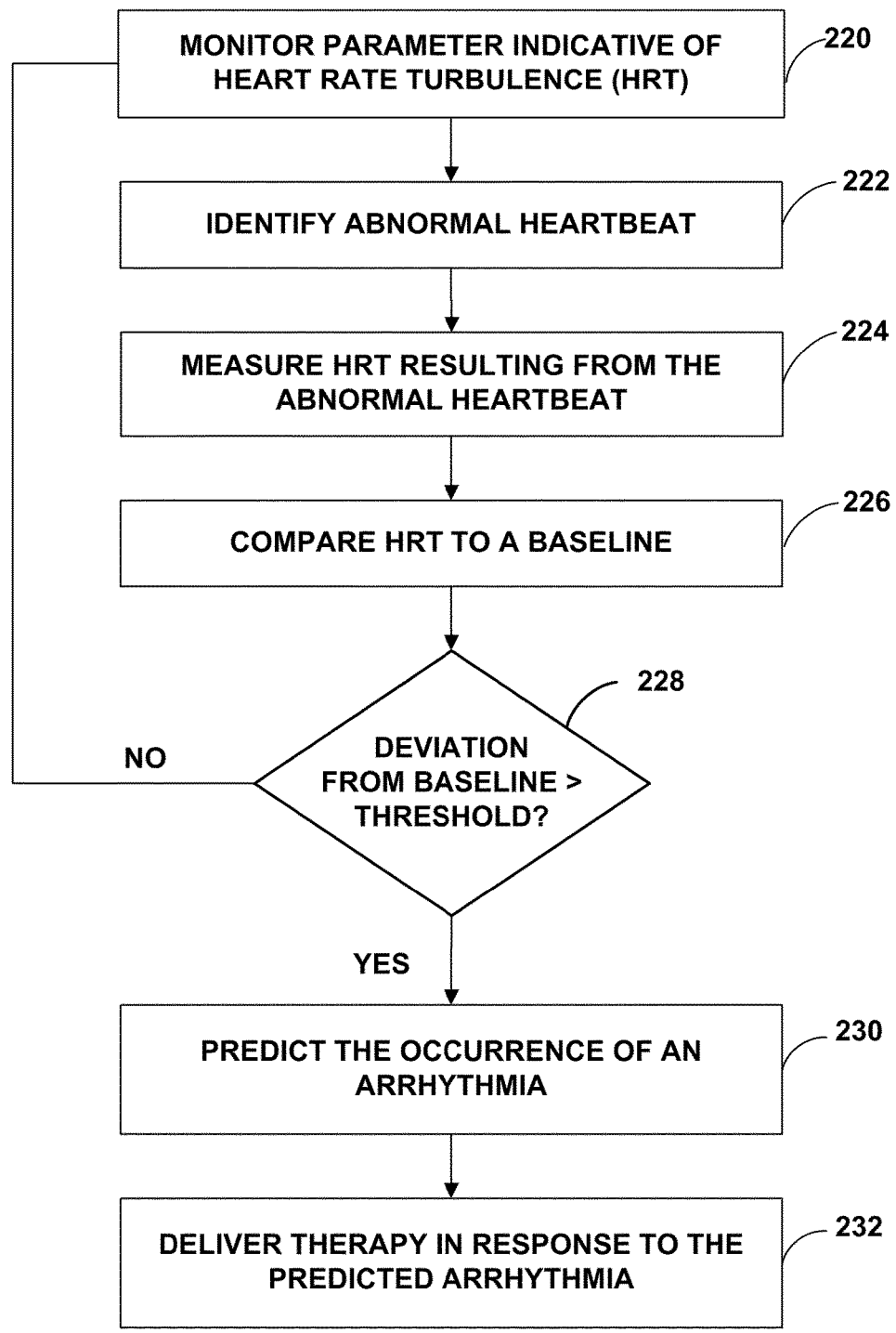
FIG. 7 is a flow diagram of an example method of predicting the occurrence of an arrhythmia based on heart rate turbulence.

FIG. 7 is a flow diagram of an example method of predicting the occurrence of an arrhythmia based on HRT. The functionality described with respect to FIG. 7 as being provided by a particular processor or device may, in other examples, be provided by any one or more of the processors or devices described herein.

Sensing module 86 may monitor a parameter indicative of HRT (220). For example, sensing module 86 may monitor an EGM signal that may be used to derive HRT. Processor 80 may identify an abnormal heartbeat (222). For example, processor 80 may analyze a signal sensed by sensing module 86 to identify abnormal heartbeats. In some examples, processor 80 may identify specific types of abnormal heartbeats that may result in detectable changes in HRT, such as PACs and/or PVCs.

Processor 80 may calculate HRT resulting from the abnormal heartbeat (224). In some examples, processor 80 may calculate turbulence onset and/or turbulence slope to quantify HRT. Turbulence onset may be calculated as the difference or ratio between one or more heart rate intervals following the abnormal heartbeat and one or more heart rate intervals preceding the abnormal heartbeat.

Figure 8:
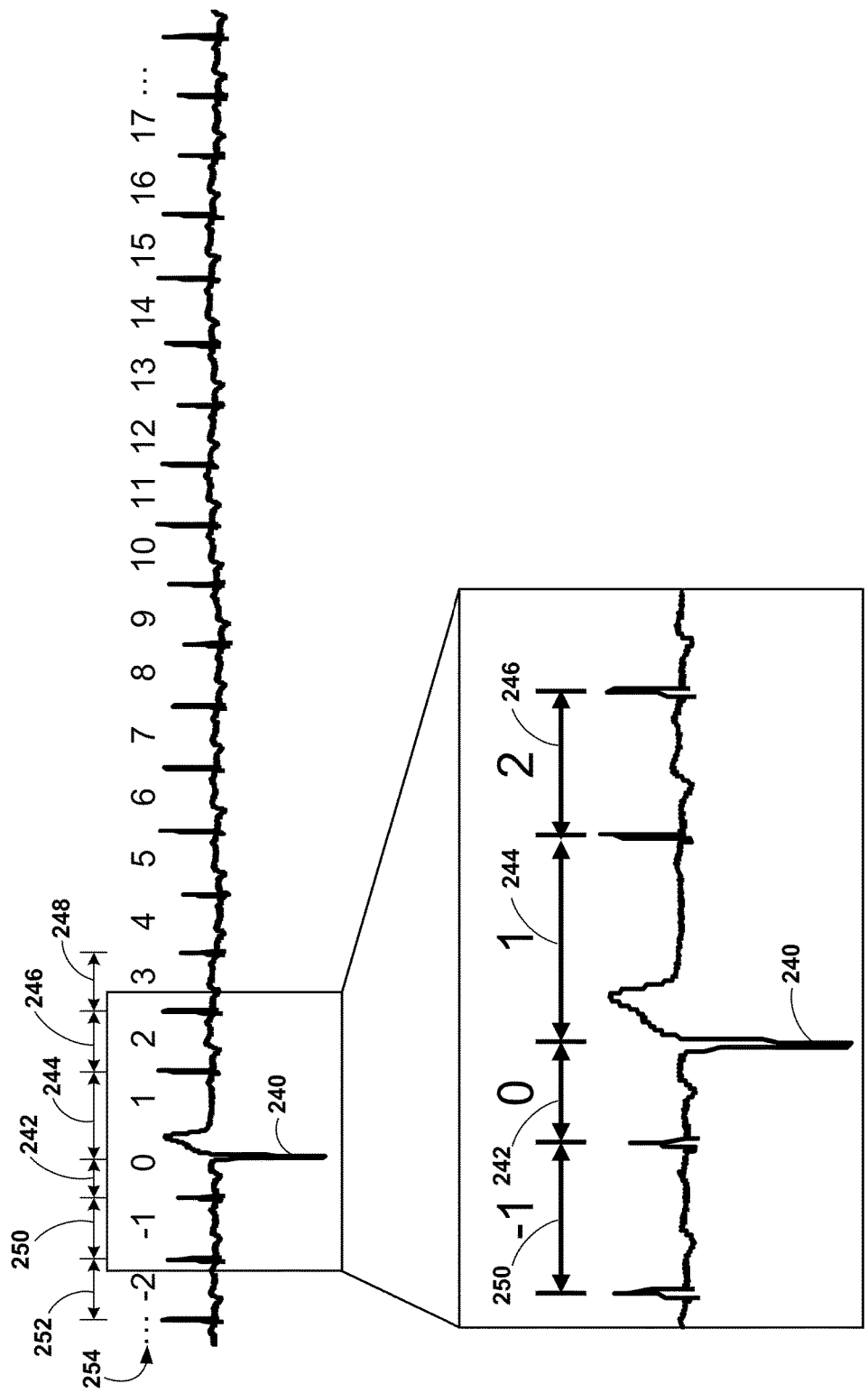
FIG. 8 is a conceptual drawing illustrating an example electrogram signal that may be used to calculate heart rate turbulence.

In the example of FIG. 8, abnormal heartbeat 240 is preceded by a shortened interval 242 and followed by a lengthened interval 244 compared to the timing intervals between heartbeats preceding abnormal heartbeat 240. Processor 80 may calculate turbulence onset by calculating the ratio or difference of the mean of the two intervals 246, 248 following the lengthened interval 244 associated with abnormal heartbeat 240 and the mean of the two intervals 250, 252 preceding the shortened interval 242 associated with abnormal heartbeat 240.

Each interval may also be referenced by an interval number 254 assigned with respect to abnormal heartbeat 240. For example, shortened interval 242 preceding abnormal heartbeat 240 may be assigned a value of zero. Other intervals may be assigned integers values based on chronological order with respect to abnormal heartbeat 240. Therefore, processor 80 may calculate turbulence onset by calculating the ratio or difference of the mean of the two intervals assigned interval numbers 2 and 3 following the lengthened interval assigned interval number 1 associated with abnormal heartbeat 240 and the mean of the two intervals −1 and −2 preceding the shortened interval assigned interval number 0 associated with abnormal heartbeat 240.

Processor 80 may calculate turbulence onset for each occurrence of an abnormal heartbeat, may calculate the average of a plurality of single turbulence onset values, or may average interval values preceding and following a plurality of abnormal heartbeats to calculate an overall turbulence onset value during an observation period.

Figure 9:
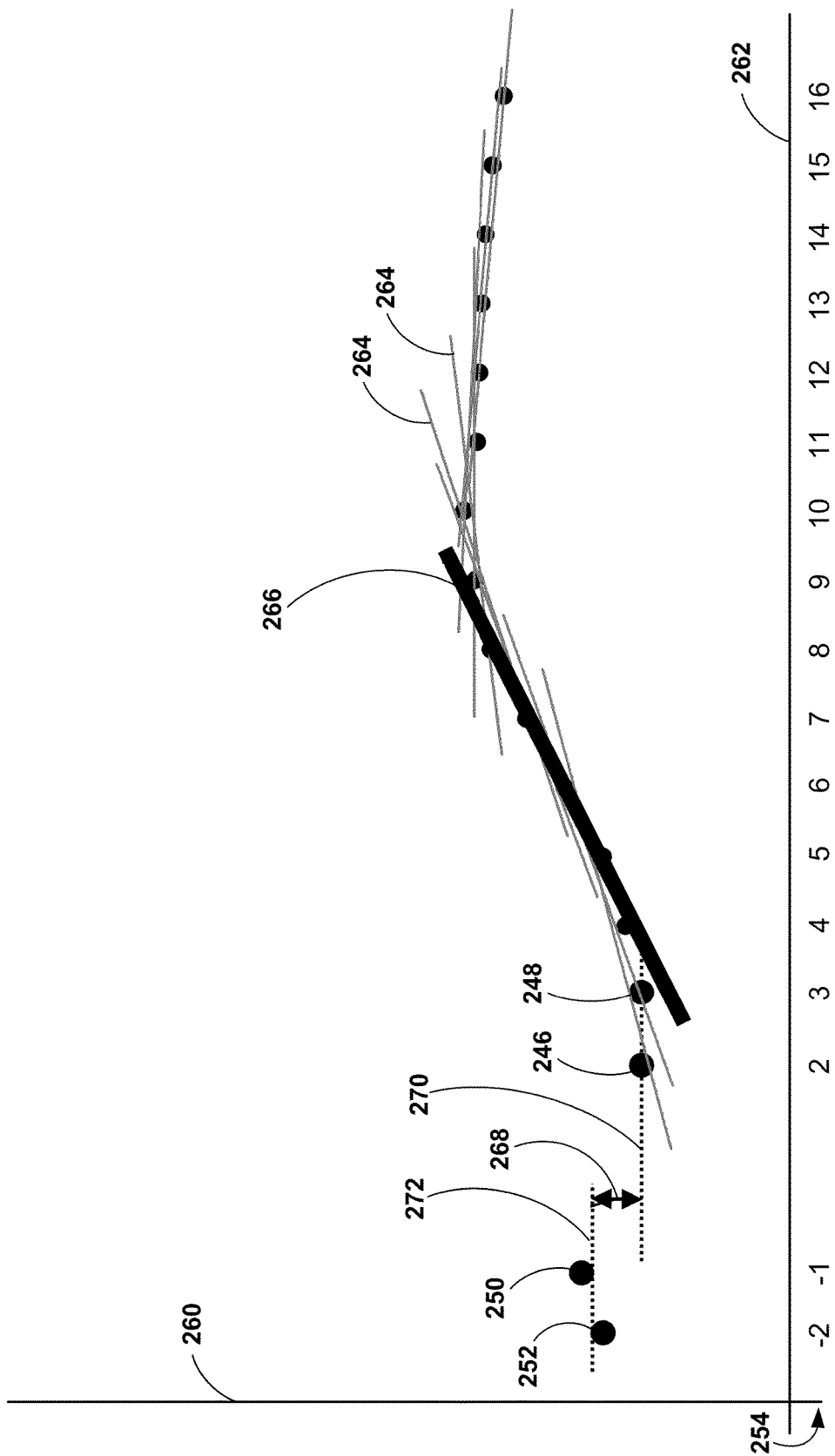
FIG. 9 is a conceptual drawing illustrating an example calculation of turbulence onset and turbulence slope.

In some examples, processor 80 may calculate turbulence slope to quantify HRT. For example, processor 80 may determine a slope based on values of heart rate intervals following an abnormal heart beat. FIG. 9 illustrates one example calculation of turbulence slope. In the example of FIG. 9, vertical axis 260 represents the time between heartbeats, e.g., interval values, in milliseconds and horizontal axis 262 represents interval numbers 254. As previously described, the shortened interval preceding abnormal heartbeat 240 may be assigned an interval number of zero and other intervals may be assigned integers values based on chronological order using interval number zero as a reference point.

FIG. 9 illustrates a plurality of regression slopes 264. Each of regression slopes 264 may fit a specified set of data points that represent interval lengths subsequent to the abnormal heartbeat. In the example of FIG. 9, each of regression slopes 264 is fit to a set of five consecutive data points selected from interval 2 through interval 16. The maximum positive slope is selected from regression slopes 264 as the slope turbulence value 266. The slope turbulence value may represent the rate at which the normal state is restored subsequent to an abnormal heartbeat. Alternate time-based techniques for quantifying HRT include measuring the time for the heart rate to return to a normal level following the abnormal heartbeat, or measuring the time from the abnormal heartbeat to the minimum or maximum interval value observed in a window of time following the abnormal heartbeat.

FIG. 9 also illustrates turbulence onset 268. The values of intervals 246, 248 following the lengthened interval associated with the abnormal heartbeat may be averaged to yield mean 270, and the values of intervals 250, 252 preceding the shortened interval associated with the abnormal heartbeat may be averaged to yield mean 272. The difference between these two means yield turbulence onset 268. In other examples, turbulence onset 268 may correspond to a ratio between mean 270 and mean 272.

In other examples, FIG. 9 may represent data from a plurality of abnormal heartbeats. In such examples, each data point may represent an average value for a respective interval number during an observation period.

Returning to FIG. 7, after HRT is calculated, the measured HRT is compared to a baseline (226). For example, turbulence onset and turbulence slope may be compared to respective baseline values. The baseline HRT may be static, or may be updated over time. For example, the baseline data may represent a mean or median value for both turbulence onset and turbulence slope observed over any appropriate number of preceding samples.

Processor 80 may determine whether the measured HRT deviates from the baseline by more than a threshold value (228). Processor 80 may require one or both of turbulence onset and turbulence slope to deviate more than a threshold amount in order to make the determination. Turbulence onset and turbulence slope may be compared to the same or different threshold values. The threshold values may be general values used for a plurality of patients or may be specified for a given patient.

If the measured HRT deviates from the baseline by more than the specified threshold, processor 80 may predict the occurrence of an arrhythmia (230). In some examples, processor 80 controls signal generator 84 to deliver a therapy configured to prevent the predicted arrhythmia from occurring, reduce an effect of the arrhythmia, or terminate the arrhythmia (232). For example, processor 80 may control signal generator 84 to deliver overdrive pacing, anti-tachycardia pacing, spinal cord stimulation, and/or vagal stimulation. Signal generator 84 may deliver a different type of therapy based on how the measured heart rate turbulence varies from the baseline.

Figure 10:
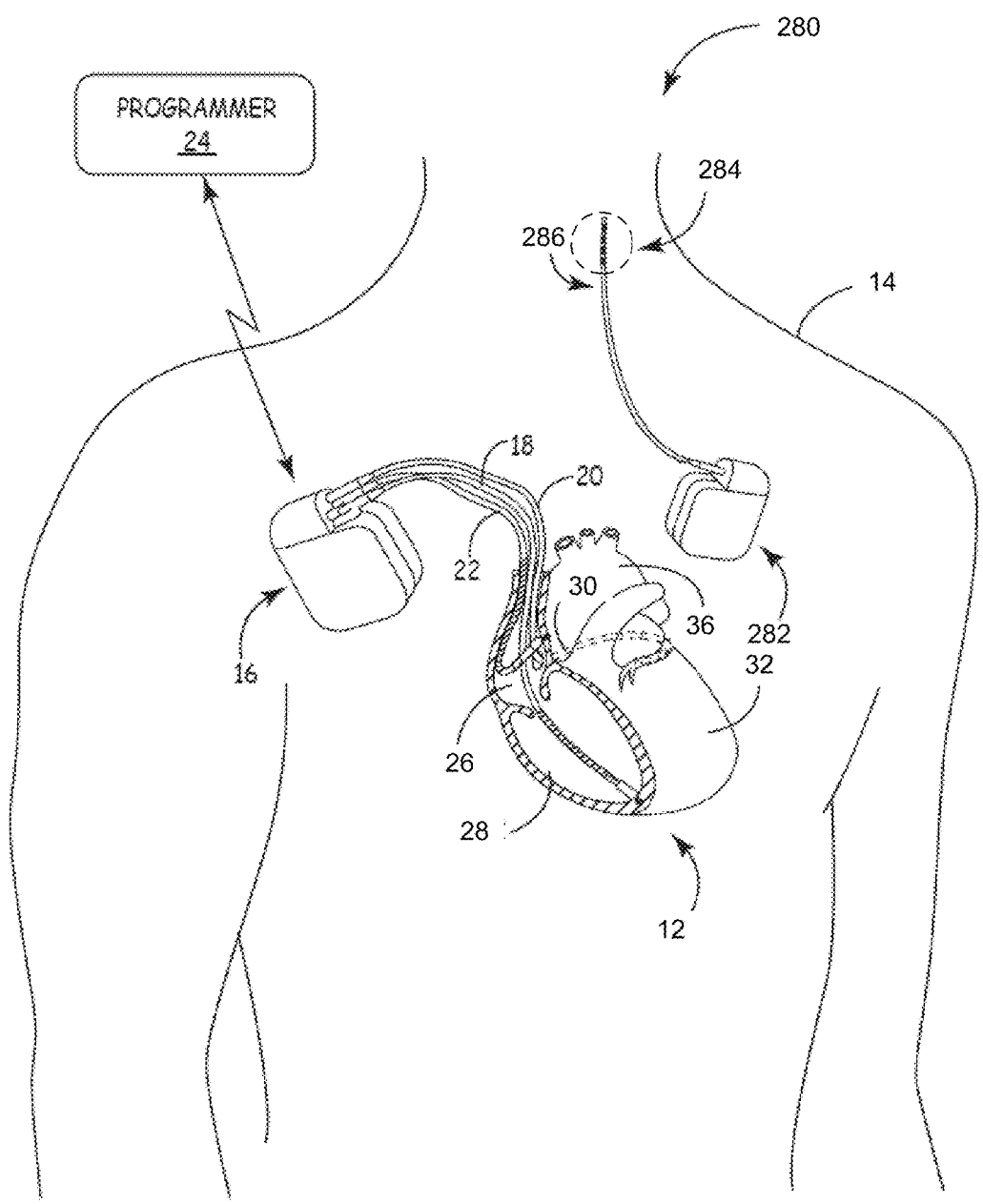
FIG. 10 is a conceptual drawing illustrating an example system that includes a neurostimulator.

FIG. 10 is a conceptual drawing illustrating an example system 280 that includes IMD 16 and IMD 282. In the example of FIG. 10, IMD 16 may be an implantable cardiac device, such as a cardiac monitoring device or an implantable pacemaker, cardioverter, and/or defibrillator. As described with respect to system 10 of FIG. 1, IMD 16 may monitor signals from and, in some examples, deliver electrical signals to heart 12. In the example of FIG. 10, IMD 282 may be a neurostimulator that delivers electrical stimulation to and/or monitors conditions associated with the brain, spinal cord, or neural tissue of patient 14. In the example of FIG. 10, IMD 282 is implanted in patient 12 proximate to target stimulation site 284, such as a tissue site proximate a vagus nerve. More particularly, lead 286 is coupled to IMD 282 and extends from IMD 282 to target stimulation site 284. Lead 286 may include one or more electrodes to sense signals from and/or deliver electrical signals to target stimulation site 284. In other examples, IMD 282 to be positioned to delivery neurostimulation to another target stimulation site, such as the brain or spinal cord.

Various examples of the invention have been described. These and other examples are within the scope of the following claims.

The invention claimed is:

1. A method comprising:
sensing cardiac contractility of a heart;
deriving a plurality of values of an interval between cardiac contractions of the heart from the sensed cardiac contractility;
measuring heart rate turbulence based on the interval values derived from the sensed cardiac contractility;
predicting an occurrence of a tachyarrhythmia based on the measured heart rate turbulence; and
delivering a cardiac stimulation therapy to the heart in response to predicting the occurrence of the tachyarrhythmia, wherein the cardiac stimulation therapy is configured to prevent the occurrence of the tachyarrhythmia.

2. The method of claim 1, further comprising
charging a therapy delivery circuit in response to predicting the occurrence of the tachyarrhythmia.

3. The method of claim 2, wherein the therapy delivery circuit comprises a circuit for delivery of a cardioversion.

4. The method of claim 3, wherein charging of the therapy delivery circuit occurs in response to the predicting of the occurrence of the tachyarrhythmia.

5. The method of claim 1, further comprising
identifying an abnormal heartbeat, wherein measuring heart rate turbulence comprises measuring heart rate turbulence resulting from the abnormal heartbeat.

6. The method of claim 5, further comprising delivering a signal configured to induce the abnormal heartbeat, wherein identifying the abnormal heart beat comprises identifying the abnormal heartbeat induced by the signal.

7. The method of claim 5, wherein the abnormal heartbeat comprises at least one of a premature atrial contraction or a premature ventricular contraction.

8. The method of claim 5, wherein measuring heart rate turbulence comprises calculating at least one of turbulence onset or turbulence slope.

9. The method of claim 5, further comprising comparing the measured heart rate turbulence to a threshold value, wherein predicting the occurrence of the tachyarrhythmia comprises predicting the occurrence of the tachyarrhythmia based on the comparison.

10. The method of claim 5, wherein identification of the abnormal heartbeat comprises identification of a naturally occurring heartbeat.

11. The method of claim 1, wherein the sensed cardiac contractility is sensed using one or more of: a sensor intracardiac or intravascular pressure, an accelerometer or other sensor capable of detecting heart or blood sounds, vibrations, or motion, an intra-cardiac or intra-arterial impedance, optical or ultrasonic sensor capable of detecting changes in blood flow associated with cardiac contractions, or an optical sensor capable of detecting oxygen saturation changes associated with cardiac contractions.

12. The method of claim 1 wherein the cardiac contractility is sensed using a sensor responsive to physical contractions of the heart.

13. The method of claim 1, wherein the therapy is configured to reduce an effect of the tachyarrhythmia or terminate the tachyarrhythmia if the tachyarrhythmia occurs.

14. A system comprising:
a sensing module that monitors cardiac contractility of a heart, the cardiac contractility being indicative of heart rate turbulence;
a processor that derives a plurality of values of an interval between cardiac contractions from the sensed cardiac contractility, measures the heart rate turbulence based on the interval values, and predicts an occurrence of a tachyarrhythmia based on the measured heart rate turbulence; and
a signal generator that provides a cardiac stimulation therapy in response to predicting the occurrence of the tachyarrhythmia, wherein the cardiac stimulation therapy is configured to prevent the occurrence of the tachyarrhythmia.

15. The system of claim 14, further comprising
a therapy delivery circuit, wherein the processer charges the therapy delivery circuit in response to predicting the occurrence of the tachyarrhythmia.

16. The system of claim 15, wherein the therapy delivery circuit comprises a circuit for delivery of cardioversion.

17. The system of claim 16, wherein charging of the therapy delivery circuit occurs in response to the predicting of the occurrence of the tachyarrhythmia.

18. The system of claim 14,
wherein the processor identifies an abnormal heartbeat and measures heart rate turbulence resulting from the abnormal heartbeat.

19. The system of claim 18, wherein identification of the abnormal heartbeat comprises identification of a naturally occurring heartbeat.

20. The system of claim 18, wherein the abnormal heartbeat comprises at least one of a premature atrial contraction or a premature ventricular contraction.

21. The system of claim 18, wherein the processor calculates at least one of turbulence onset or turbulence slope.

22. The system of claim 18, wherein the processor compares the measured heart rate turbulence to a threshold value and predicts the occurrence of the tachyarrhythmia based on the comparison.

23. The system of claim 18, wherein the processor comprises a processor of a programming device.

24. The system of claim 18, wherein the processor comprises a processor of a medical device.

25. The system of claim 24, wherein the medical device comprises an implantable medical device.

26. The system of claim 24, wherein the medical device comprises an external medical device.

27. The system of claim 14, wherein the sensing module comprises one or more of: a sensor intracardiac or intravascular pressure, an accelerometer or other sensor capable of detecting heart or blood sounds, vibrations, or motion, an intra-cardiac or intra-arterial impedance, optical or ultrasonic sensor capable of detecting changes in blood flow associated with cardiac contractions, or an optical sensor capable of detecting oxygen saturation changes associated with cardiac contractions.

28. The system of claim 14 wherein the sensing module comprises a sensor responsive to physical contractions of the heart.

29. The system of claim 14, wherein the signal generator provides the therapy configured to reduce an effect of the tachyarrhythmia or terminate the tachyarrhythmia if the tachyarrhythmia occurs.

* * * * *